United States Patent
Sekendur

[19]

[11] Patent Number: 6,079,981

[45] Date of Patent: Jun. 27, 2000

[54] ONE VISIT DENTURE

[76] Inventor: Oral Fatih Sekendur, 399 W. Fullerton Pkwy., #15 W, Chicago, Ill. 60614

[21] Appl. No.: 08/106,397

[22] Filed: Aug. 12, 1993

Related U.S. Application Data

[63] Continuation-in-part of application No. 07/767,504, Sep. 30, 1991, abandoned.

[51] Int. Cl.$^7$ .............................. A61C 13/00; A61C 13/08
[52] U.S. Cl. ........................ 433/171; 433/191; 433/202.1
[58] Field of Search .................................... 433/191, 193, 433/195, 202.1, 171

[56] References Cited

U.S. PATENT DOCUMENTS

| | | | |
|---|---|---|---|
| 908,627 | 1/1909 | Telle | 433/191 |
| 1,227,602 | 5/1917 | Fogg | 433/191 |
| 1,615,034 | 1/1927 | Pryor et al. | 433/191 X |
| 1,714,185 | 5/1929 | Morgan | 433/191 X |
| 2,269,780 | 1/1942 | Myerson | 433/26 X |
| 2,641,802 | 6/1953 | Grant | 433/191 X |
| 3,343,262 | 9/1967 | Burg | 433/191 X |
| 3,958,333 | 5/1976 | Heimansohn | 433/191 |

*Primary Examiner*—Nicholas D. Lucchesi

[57] ABSTRACT

This invention provides a method for making a customized denture from standardized segments of prefabricated prosthetic teeth which may be joined in an adjustable fashion to suit an individual oral cavity. The prosthetic tooth comprises a denture tooth bonded to its individual gum segment to form a prosthetic tooth. The gum segment forms the gum line and simplifies denture fabrication by practically eliminating the time consuming and difficult task of hand forming the gum line during the setup process. A plurality of prosthetic teeth may be adjustably joined in a lateral and/or occlusal relationship. The prosthetic teeth may be adjustable, interchangeable, and joinable with one another to suit an individual oral cavity. The array of prosthetic teeth is selected that most closely suits an individual oral cavity, then evaluated in the mouth of the patient by the dentist and the patient for the mold and shade. Next, the selected prosthetic teeth are conformed in the mouth or on a model representation of the mouth to form a denture. Finally, the denture is cured and finished.

20 Claims, 4 Drawing Sheets

ONE VISIT DENTURE

This application is a continuation-in-part of U.S. Ser. No. 07/767,504, filed Sep. 30, 1991, now abandoned.

BACKGROUND—FIELD OF INVENTION

This invention relates to the art and science of dental prosthetics whereby dental professionals can produce a high quality complete denture, a partial denture, and related devices at a substantially reduced cost by reducing or eliminating at least on of the following conventionally required components of production: (a) time, (b) level of technical skill, © expensive and complicated dental equipment, (d) expensive materials, and (e) labor.

BACKGROUND—DESCRIPTION OF PRIOR ART

The following United States Patents are believed to be most closely related to the present invention:

| U.S. Pat. Nos. #08/106,397: ORAL SEKENDUR, 399 W. FULLERTON PKWY., CHICAGO, IL 60614 Tel.: (773) 880-5574 | | | |
|---|---|---|---|
| 3,083,459 | 3,241,238 | 3,460,252 | 3,464,111 |
| 3,621,575 | 3,667,123 | 3,727,309 | 3,783,514 |
| 3,813,777 | 3,838,513 | 3,839,796 | 4,012,838 |
| 4,175,322 | 4,184,253 | 4,247,287 | 4,337,042 |
| 4,345,900 | 4,370,133 | 4,457,713 | 4,470,815 |
| 4,551,098 | 4,583,947 | 4,657,509 | 4,681,543 |
| 4,705,476 | 4,838,789 | 4,017,971 | 4,097,992 |
| 4,371,339 | 4,521,193 | 4,551,098 | 4,583,947 |
| 4,681,543 | 4,705,476 | 4,865,546 | 4,981,437 |
| 5,049,075 | 5,304,062 | 5,304,062 | 5,380,203 |
| 5,502,087 | 5,676,546 | | |

Aesthetically pleasing, healthy, and functional teeth are an important part of a person's physical and mental health. Many people suffer the unfortunate consequences of physical and emotional pain and discomfort due to unhealthy or missing teeth. This situation can cause many problems such as impairment of the natural function of mastication, speech defects, distorted facial contour, and general discomfort. In addition, headaches, referred pain to other parts of the body, and other illnesses are related to unhealthy or missing teeth. Therefore, repair or replacement of impaired teeth is crucial to general mental and physical health.

Dentures are conventionally constructed by the dental technician and fitted by the dentist using the flask investment technique. This complex process requires the measurement of masticatory function, impressions of the teeth and surrounding tissue of the affected area, study models and working models, and a series of involved and complicated steps by the dentist and dental technician to manufacture the denture. The entire process requires numerous appointments between the dentist and patient. It also involves a significant amount of time and skill. The denture makes numerous round trips between the dental office and the dental laboratory. This subjects the denture to the usual hazards of long distance transportation and communication. The amount of skill, effort and time conventionally required to produce a functional, aesthetically pleasing and quality denture is significant. Additionally, aesthetic control and fit due to the distortion of the dental materials are compromised.

Conventional dentures are made in four or five office visits to the dentist and generally require the following steps:

I. First Visit
  A. Dentist
    1. Examine Patient
    2. Take Preliminary Alginate Impressions
  B. Laboratory
    1. Cast Mold
    2. Make Custom Impression Trays
II. Second Visit
  A. Dentist
    1. Check and Adjust Impression Trays
    2. Take Final Impressions
  B. Laboratory
    1. Cast Master Mold
    2. Stabilize Baseplate
    3. Wax Occlusal Rim
III. Third Visit
  A. Dentist
    1. Determine Maxillo-mandibular Relation
    2. Select Teeth
    3. Take Bite Registration
  B. Laboratory
    1. Set Anterior and Posterior Teeth
    2. Wax Complete Denture for Try-In
VI. Fourth Visit
  A. Dentist
    1. Check Aesthetics and Functionality
    2. Check Occlusal and Vertical Dimension
    3. Make Necessary Corrections
  B. Laboratory
    1. Make Necessary Corrections
    2. Process and Finish
V. Fifth Visit
  A. Dentist
    1. Check and Correct Occlusion
    2. Finish and Deliver Some practitioners have been able to reduce the five-appointment denture to a three-appointment denture. This is the subject matter of an article entitled *The Three Appointment Denture Technique as Presented by Robert H. Griffiths, D.D.S. and Don Kaylor, C.D.T.* printed by the Council on Prosthetic Services and Dental Laboratory Relations in May, 1979 in a booklet entitled *Compilation of Reduced Fee Denture Techniques*. The article describes the three-appointment denture:

The cost saving factors of this technique depend on close cooperation between the dentist and the dental laboratory.
I. First Sitting (Should not exceed 45 minutes)
  A. Examination of tissue and structures involved with denture construction.
  B. Radiographic examination—panoramic radiograph ideal for edentulous patients.
  C. Ascertain patient history and mental attitude toward dentures.
  D. Evaluation of patient as candidate for this technique.
  E. Selection of impression trays—we utilize the accu-dent trays.
  F. Facial Measurements
    1. Dent-profile scale measurement
    2. Dentsply face bow measurement
    3. Alameter reading
    4. Papillameter measurement
  G. Tentative Vertical and centric relationship
    1. Use of insta-mold for bite establishment
    2. Recording of mid-line and lip line H. Tooth and Shade Selection
  1. Mold of upper anterior tooth preferred
  2. Selection of brand of anterior tooth
  3. Selection of posterior mold
  4. Selection of brand of posterior tooth
I. Completion of Work Order
  1. Recording of all measurements of the face previously taken
  2. Recording of mold, shade and type of tooth preferred in anterior and posterior
  3. Any other information required to complete the denture.

The dentist should receive stabilized base plates from the laboratory for the upper and lower jaw. All lower teeth should be set and properly waxed on the lower base plate. The six upper anterior teeth should be waxed into proper position and arrangement and bite blocks should be on the posterior areas of the upper base plate.

II. Second Sitting (Should not exceed 20 minutes)
  A. Try-in of setup received from our laboratory
    1. Check the tooth arrangement and esthetics
    2. Check phonetics
    3. Have patient acceptance of setup
    4. Adjust upper bite block to attain the proper vertical dimension
    5. Record proper centric relationship
  B. Return bit rims with setup and occlusal record to laboratory with properly completed work order form.

The dentist should receive completed upper and lower dentures from the dental laboratory.

III. Third Sitting (Should not exceed 20 minutes)
  A. Placement of upper denture
    1. Check fit of base with pressure indicator paste
    2. Check esthetics
    3. Check border extensions
  B. Placement of lower denture
    1. Check fit of base with pressure indicator paste
    2. Check extensions of borders
    3. Check esthetics
    4. Check phonetics
  C. Check and balance occlusion
    1. Carbon paper markings
    2. Occlusal wax recordings—Kerr occlusal indicator wax
  D. Instructions to the Patient
    1. How to chew
    2. How to bite
    3. How to stabilize and retain lower denture
    4. How to overcome impaired speech
    5. What to do for "sore spots"
    6. Follow up and recall needs.

The fabrication of the wax setup ready for try-in from the dental laboratory requires a significant amount of time and skill. The process is basically two fold: placing the denture teeth in proper orientation to fit a particular oral cavity and, contouring wax around the denture teeth to appear lifelike. Assuming the denture teeth are setup in proper orientation, the booklet entitled *Anatomical Waxup Techniques* (VIDENT, Baldwin Park, Calif.) describes in 26 steps the difficult process of contouring wax to appear lifelike:

1. Look at any cast in your laboratory and you will find some basic anatomical similarities: a gingival roll over the centrals, the canine has a 5–7 degree gingival/incisal slope so the root protrudes to give a canine eminence. Teeth have a free gingival margin, or roll much like tissue around a fingernail.

2. The trifurcated roots and the structure over the molar create a buccal eminentia. Note that the teeth are encased in tissue not back behind. The inter dental papillae is full and rounded, regardless of its height, so that the lips and tongue can evacuate food from the area.

Establishing the Thickness of the Denture

3. Before beginning the wax-up for the denture base, cut the land area down to the thickness desired and place a pencil mark on the cast at that depth. (When waxing a try-in the extension of the base plate is the border.)

4. Cut a 3–4 millimeter ribbon of wax to begin laying on the base foundation.

5. Double over this ribbon to produce a thicker roll—approximately 3 millimeters in diameter—and position just above the pencil border line.

6. With a heated instrument, seal this roll onto the cast—establishing the thickness of the denture base and minimizing the grinding and finishing required at completion. The remaining waxing will be anatomical veneering from the periphery to the teeth.

Creating the Basic Anatomy

7. The buccal eminentia and the canine eminence are developed first. Use a cold spatula to remove wax between the teeth and to form the root under structure.

Veneering Under structure To Stimulate Natural Anatomy

8. Cut a piece of softened base plate wax for wrapping the under structure and the teeth.

9. Heat the under structure before veneering with the base plate wax to insure complete adherence.

10. Adapt the wax into the inter proximal spaces and around the under structure—eliminating air bubbles.

11. Merge the labial wax with the peripheral wax. Note that the denture base is already taking on lifelike anatomy—without any carving of the veneered wax layer.

12. When softening wax after the labial veneer has been applied, hold the case at least 12" above the burner.

Exposing the Teeth and Creating Gingival Roll

13. Using a No. 7 spatula, clear the wax from the face of the teeth while leaving it in the inter dental areas. This is easier if you hold the spatula as parallel as possible to the tooth surface as you work. The inter dental wax must remain in place at this time.

14. Finish the wax removal by drawing the large end of the No. 7 spatula through the wax until you feel contact with the gingival bulge that is on every denture tooth, then clear away the long axis of the tooth.

15. Work toward the proximal—exposing only the face of the tooth and leaving the inter dental areas untouched. The papillae should be kept full and intact.

16. When the wax has been cleared from the tooth, the gingival will be very jagged and irregular. Use the small end of the No. 7 spatula to smooth and give more definition.

Creating a Natural Papillae

17. Cut off the tip of the papillae according to the age of the patient using a Hollenbeck or similar right angle carver. (See notes on Aging of the Inter dental Papillae.)

18. Lay the broad area of this instrument against the wax and draw it down toward the base along either side. This makes the wax roll between the teeth.

19. Create a gingival flap, or free gingival margin around each tooth by removing a small amount of wax with the Hollenbeck carver.

20. At this time the gingival margin will be flat. As previously illustrated, use the flame to soften the surface of the wax and roll the margin downward with your thumb. This rolling will prevent food from packing against this area on the finished denture.

21. Rolling of the gingival margin will carry some wax debris down onto the flange. This debris can be easily burnished off revealing the anatomy you had before—do not re-carve.

Natural Stippling Technique

22. To avoid the unnatural effects of direct stippling, try the following. Lay a sheet of polyethylene over the wax and then roll a stiff bristle, tooth cleaning brush back and forth over the covered wax-up. The polyethylene sheet will make the stipple holes rounded depressions rather than jagged holes which can more easily collect calculus, plaque and bacteria.

Aging of the Inter dental Papillae

23. Youthful patients in their twenties will have papillae which are long, full and healthy.

24. Middle-aged patients in their forties or fifties have papillae which end approximately a millimeter above the proximal contact of the tooth. Another aging technique is to use the spoon end of a Lacrone carver to create a little periodontal involvement over the tooth in one area (not completely around.)

25. For patients seventy-five or older, cut the papillae wax at least three millimeters above the proximal contact of the tooth. Notice that the process and inter dental papillae are still full, heavy and rounded so that the lips and tongue can evacuate food. When a space is opened up like this, a sluice way is provided so the food can push through to the lingual of the denture.

26. If the simple, straightforward technique explained and illustrated is followed, the completed wax-up will simulate natural anatomy.

Save for step 22, in the above described technique, steps 7–25 describe the formation of the gum line. The formation of the gum line may comprises 30–50% of the setup time. This complex and time consuming process can be avoided by using the method described in the present invention.

The cost of a hand-crafted and quality denture is very high because fabrication involves much time, skill, expensive dental equipment, and expensive materials.

Many of the difficulties in producing a denture cheaply, quickly, and easily are due to the great diversity of size, shapes, and colors of dental patients' teeth, mouths, and facial features requiring custom fabrication of each denture and making standardization of prefabricated dentures impractical.

Previous attempts to overcome the shortcomings of the above described conventional methods have met with little success. The problem lies in the difficulty of customizing a denture to an individual oral cavity. Some important areas of difficulty for a customized fit are the edentulous ridge, palatal area and occlusion. Previous techniques utilizing partially prefabricated dentures have not had much success.

In general, partially prefabricated dentures consist of thermoplastic prefabricated denture base, available in a number of sizes and shapes, with attached teeth that offer a small variety of mold and shade selection. Once selected, the prefabricated denture base is heated and adapted to the individual patient, and then relined for better fit.

Many proposals suggested combining a rigid structure with a soft deformable structure in an attempt to customize a denture. They employed a hard base structure of cured acrylic plastic on which hard acrylic denture teeth were permanently bonded. As a substructure, a liner layer of soft uncured acrylic plastic was attached to the tissue-side of the hard layer. The entire structure was impression fitted in the mouth of a dental patient whereby the soft liner layer was intended to conform intimately to an individual oral cavity. Since the hard base structure did not allow for any deformation, dentures were only partially customized. This was possible in limited instances where the shape of the edentulous ridge was in general conformity with the shape of the hard base structure of the stock denture. The palatal area of the stock denture did not fit except in rare instances where the shape of the patient's palate was almost identical to that of the stock denture. Mostly, the palatal area of the finished denture was too thick, too thin, or impinged on the tissue causing pain and discomfort. The occlusion was even more difficult to adapt.

In an attempt to more closely conform with the palatal area, some proposals provided for a deformable metal mesh embedded in an elastomeric environment as part of a rigid u-shaped frame structure. This approach offered slightly more accommodation to the larger contours of a greater variety of palatal structures. However, the denture did not conform to the smaller contours of the ridged portion of the cavity causing pain and discomfort to the patient.

Other proposals provided for prosthetic human teeth to be embedded in a negative impression of a denture. The impression was filled with soft uncured denture material, fitted in the mouth over the edentulous ridge and palatal area, and allowed to harden. The hardened denture, now bonded to the teeth, was removed from the impression tray and finished. This approach allowed for a better fit on the tissue-side of the denture. However, it did not allow for evaluation of the teeth in the patient's mouth before curing. Thus, the selection of teeth for shade and mold for a proper aesthetic and functional match to an individual patient was not possible. Further, the thickness of the denture in the gum and palatal area was not controlled well. Thus, some dentures were too thick causing discomfort. Still others were too thin and fragile. Still further, this method did not provide for an accurate way to determine occlusion.

Still other proposals allowed for an acceptable denture to be produced on a model representation of an individual oral cavity. Although reasonably successful, this approach did not save much time and expense, in that, it did not deviate significantly from the conventional investment flask method described above. At the least, the process still required (a) measuring the masticatory function, (b) impressions of the teeth and surrounding tissue of the affected area, © study and working models, (d) placing teeth in their proper relationship to one another on the model, (e) curing the denture out of the mouth, (f) more than one office visit, (g) transporting back and forth to a dental laboratory, (h) in some cases, investing and pressure molding the denture, and (I) curing with heat and pressure for a long period of time. In addition, in some instances, this process did not allow for the evaluation and selection of teeth in the mouth of a dental patient. Thus, it had the potential for poor aesthetic results.

More recently, since the advent of light curable dental materials, procedures and apparatus have been developed which utilize these materials. This is the subject matter of several patents assigned to Dentsply International of York, Pa. including U.S. Pat. Nos. 4,533,325, 4,551,098, 4,609,351, 4,681,543, and 4,705,476. Another recent patent (U.S. Pat. No. 5,676,546) uses a woven fabric sandwiched in a compost laminate and formed on a model representation of the dental patient's mouth. Although these patents have eliminated the use of the flask investment technique due to the use of light curable dental materials, they still incorporate most of the aforementioned conventional steps without any significant time savings or quality improvement. Thus, the use of light curable dental materials described in the patents above have not been widely accepted for denture fabrication.

Save for the present invention, most of the above methods of denture fabrication use two essential materials: plaster/stone and wax. To work successfully with both of these materials requires a great deal of skill and experience. Further, these materials can be very messy and difficult to work with. Most of the above methods require model representations of the individual patient's mouth to be mounted on an articulator. The present invention does not need to use plaster/stone or wax, and does not require model articulation.

In summary, the shortcomings of prior proposals to overcome some of the difficulties of producing a conventional custom denture are:

1. poor fit to the tissue area of an individual patient,
2. poor fit to the bite of an individual patient,
3. poor aesthetic conformity to an individual patient,
4. poor functionality,
5. poor quality and life of the denture,
6. excessive thickness or thinness of the denture base,
7. expensive, complex, and time consuming production process,
8. use of plaster/stone and wax,
9. use of articulated models
10. high skill level requirement.

The present invention overcomes all of the aforementioned shortcomings by providing a denture device that is completely, accurately, and comfortably conformable to an individual oral cavity. It is easily, quickly, and entirely produced by the dentist, with or without the help of the dental technician, with only a few pieces of equipment, directly on a working platform comprising the mouth or a model representation of the mouth of a dental patient, in just one dental visit.

In summary, the present invention substantially reduces the cost and time conventionally required to produce a custom denture, and eliminates the need to transport the denture between the dental office and the dental laboratory. The aforementioned previous methods have been unsuccessful, in that, they have not been widely accepted as a means to produce dentures.

Objects and Advantages

It is a primary object of the present invention to provide a prosthetic tooth different from a conventional denture tooth in that the prosthetic tooth comprises a denture tooth joined to a gingival apron conforming in appearance to natural gum tissue, being joined to the denture tooth at the gum line, extending along at least a part of the gum line, and extending away from the gum line to the degree that setting-up at least one prosthetic tooth to form a denture is possible.

An additional primary object of the present invention is to provide a prosthetic tooth comprising a pre formed gum line. The pre formed gum line comprises the part of the gingiva at the gingival margin or gum line which is already joined to the denture tooth. The gingiva is segmented at the inter proximal so as to enable individual setup. A small space at the juncture between the prosthetic teeth at the inter proximal is allowed for adjustment of the prosthetic teeth and may need to be filled in during set up. This should be a simple process requiring very little time and skill. In addition, the prosthetic tooth comprises a pre formed gum line which does not extend completely into the area of the papillae, thus enabling adjustment of the height of the papillae to accommodate the age of the patient during set up.

Another primary object of the present invention is to provide a technique for fabricating dentures rapidly and simply with the use of the aforementioned prosthetic teeth.

Yet another primary object of the present invention is to provide a technique for fabricating dentures rapidly and simply with the use of the aforementioned prosthetic teeth and light-curable dental materials.

Still another primary object of the present invention is to provide a method of producing and fitting a denture comprising providing a working platform, which may already contain some teeth, where the working platform is selected from the group consisting of the mouth of a dental patient, a model representation of the mouth of a dental patient, the mouth of a dental patient containing an already prepared prosthesis, and a model representation of the mouth of a dental patient containing an already prepared prosthesis.

An additional object of the present invention is to provide a method of producing and fitting a denture whereby the prosthetic denture is produced and fitted almost entirely on the working platform.

Another object of the present invention is to provide an improved and less expensive customized denture.

Yet another object of the present invention is to enable the dentist to fabricate the denture entirely in the dental office without the use of a commercial dental lab.

A still further object of the present invention is to provide an improved and less expensive customized denture where the steps of fabrication include:

a. providing a working platform, which may already contain some teeth, where the working platform is selected from the group consisting of
   the mouth of a dental patient,
   a model representation of the mouth of a dental patient,
   the mouth of a dental patient containing an already prepared prosthesis,
   and a model representation of the mouth of a dental patient containing an already prepared prosthesis;
b. providing at least one prosthetic tooth comprising a denture tooth; and a gingival apron conforming in appearance to natural gum tissue, being joined to the denture tooth at the gum line, extending along at least a part of the gum line, and extending away from the gum line to the degree that setting-up at least one prosthetic tooth to form a denture is possible;
c. providing a denture base to fit the working platform;
d. setting-up at least one prosthetic tooth on the denture base to fit the working platform;
e. forming the denture to final form;
f. processing and finishing the denture.

Still another object of the present invention is to provide an improved and less expensive customized denture where the number of patient appointments are reduced from as many as six to as little as one.

It is a further object of the present invention to provide an improved and less expensive method of making a custom denture.

It is still a further object of the present invention to provide a method of making a custom denture at a lower cost through the reduction of the amount of time, the amount of labor, the level of technical skill, the use of expensive equipment, and the use of expensive materials conventionally required to make custom dentures.

A further object of the present invention is to reduce the number of steps conventionally required to produce a quality denture.

Still another object of the present invention is to reduce the level of technical skill conventionally required to make a quality denture.

Moreover, this invention provides a lower cost custom denture by eliminating or reducing the use of some of the expensive equipment required by the prior art.

Still further, this invention provides a lower cost custom denture by reducing the amount of time conventionally required to fabricate the denture.

Further, this invention provides a lower cost custom denture by reducing the amount of labor conventionally required to fabricate the denture.

Yet another object of the present invention is to reduce the number, cost, and difficulty of operation of dental equipment conventionally required to produce a quality denture.

A further object of the present invention is to reduce the use of expensive materials conventionally required to make a quality denture.

Another object of the present invention is to eliminate or reduce the number of times the denture is conventionally shipped back and forth to the dental laboratory.

It is an object of the present invention to provide an improved custom denture which can be fitted, produced, and finished entirely by the attending dentist who is always controlling the quality of the denture.

It is a further object of the present invention to provide an improved method of making a custom denture with greater cosmetic value wherein part of the denture is produced from a master mold to ensure that the anatomical detail is transferred to each denture.

Another object of the present invention is to provide an improved denture and method of making a custom denture with greater cosmetic value wherein the denture is partially prefabricated.

A still further object of the present invention is to provide an improved method of making a custom denture with greater cosmetic value wherein the prosthetic teeth are evaluated and selected for accurate fit and aesthetic value in the mouth of the patient by the dentist and the patient.

Further, another object of the present invention is to provide an improved method of making a custom denture with greater functionality wherein the teeth are set to accurate occlusion in the mouth of the patient by the dentist before curing.

Another object of the present invention is to provide an improved method of making a custom denture by allowing the dentist to adjust the prosthetic teeth directly in the mouth of the patient, thus eliminating the guesswork of setting-up teeth on a model representation by the dental technician who does not have the advantage of evaluating the teeth in the mouth of the patient.

Yet another object of the present invention is to provide an improved method of making a custom denture which requires not a single impression and may require only one impression if the dentist elects to have the dental laboratory produce or finish the denture.

Another object of the present invention is to substantially reduces the patient's chair time to approximately one to two hours.

A still further object of the present invention is to improve the method of positioning prosthetic teeth on a denture base.

Yet another object of the present invention is to provide an apparatus for maintaining a plurality of prosthetic teeth in an adjustable occlusal relationship.

Still another object of the present invention is to provide an apparatus for maintaining a plurality of prosthetic teeth in a fixed occlusal relationship.

Another object of the present invention is to save time by eliminating the need to carve much of the anatomical detail in a wax setup.

Another object of the present invention is to save time by allowing a plurality of prosthetic teeth to be setup simultaneously.

It is yet another object of the present invention to enable standardized prefabricated dentures to be adjustable enough to make a quality custom denture which fits accurately and comfortably to an individual oral cavity.

According to a broad aspect, this invention provides a method for making a customized denture from standardized segments of prefabricated prosthetic teeth which may be joined in an adjustable fashion to suit an individual oral cavity. Each denture tooth is bonded to its own separate small and thin gum segment to form a prosthetic tooth. A plurality of prosthetic teeth may be in turn optionally and adjustably connected in a lateral and/or occlusal relationship. The prosthetic teeth may be adjustable, interchangeable, and connectable with one another to suit an individual oral cavity. The array of prosthetic teeth is selected that most closely suits an individual oral cavity, then evaluated in the mouth of the patient by the dentist and the patient for the mold and shade. Next, the selected prosthetic teeth are conformed in the mouth or on a model representation of the mouth to the surface contours of the edentulous ridge and palatal area, to the desired bite, and to any other structures in the mouth. Finally, the denture is cured and finished.

Still another object of the present invention is to provide a multiplicity of modular prefabricated prosthetic teeth in various arrangements of various standard molds and shades that are adjustable, interchangeable, and connectable with one another for fitting an individual oral cavity.

Another object of the present invention is to enable the prosthetic teeth to be adapted, and the denture to be produced, directly in the patient's mouth or on a model representation of at least a portion of the oral cavity.

In a further aspect, this invention provides a method of adjusting and fitting the prosthetic teeth to the desired relationship by an adjusting means such as a knob-shaped, button-shaped, or loop-shaped structure on an accessible surface for catching with an instrument and moving the prosthetic teeth.

In another aspect, this invention provides a method of adjusting the prosthetic teeth to the desired relationship by a means for joining the prosthetic teeth in a configuration consistent with natural human dentition.

According to a further aspect, this invention provides a method of adjusting the prosthetic teeth to the desired relationship by means of an alignment plate.

According to a still further aspect this invention provides for a prefabricated set of complete upper and lower prosthetic teeth to be preset and attached in centric registry to an alignment plate with the desired occlusal relationship whereby the teeth remain fixed in place until adjusted by the dentist.

A still further aspect this invention provides for a flexible film formed on the prosthetic teeth or the prefabricated denture device.

A further aspect this invention provides for prosthetic teeth to be joined by a deflectable string-shaped structure which is securely and unobtrusively attached to each prosthetic tooth and may allow the connection between the prosthetic teeth to be maintained even if one or more prosthetic teeth in a set have to be adjusted, removed, or replaced to accommodate an individual oral cavity.

DESCRIPTION OF THE DRAWINGS

FIG. 3a is a perspective view of a tooth card comprising prosthetic teeth FIG. 3b a cross sectional view showing parts of a denture on a working platform FIG. 4b is a perspective view of a tooth card comprising prosthetic teeth with a pliable base FIG. 4c a cross sectional view showing parts of a denture on a working platform

DESCRIPTION OF THE PREFERRED EMBODIMENTS a) Prosthetic tooth

Figures 1, 2:
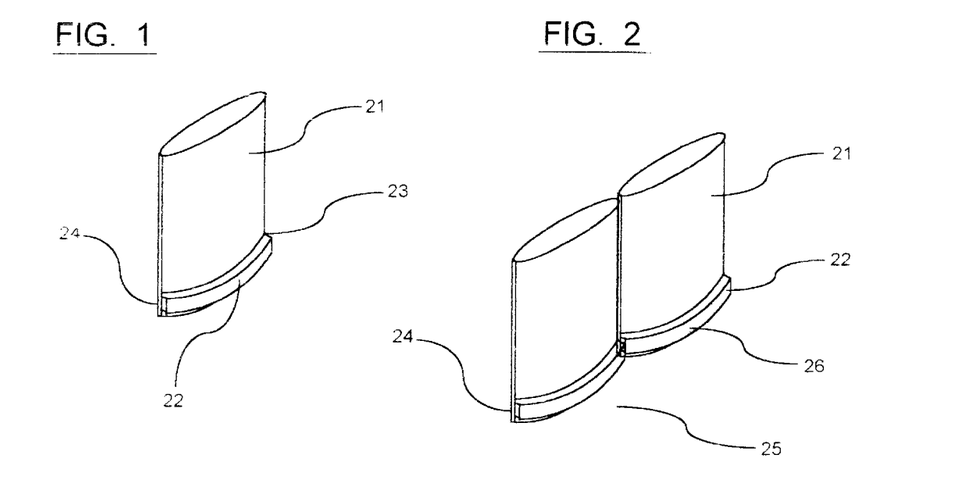
FIG. 1 is a side view of a prosthetic tooth comprising a denture tooth and a gingival apron
FIG. 2 is a facial view of two upper central teeth showing the inter proximal plane and a joining means

FIG. 1 illustrates an example of a prosthetic tooth comprising a denture tooth 21 and a gingival apron 22. The denture tooth is comprised of a conventional artificial tooth for dentures commercially available in various molds and shades. The gingival apron conforms in appearance to natural gum tissue, being joined to the denture tooth at the gum line 23, extending along at least a part of the gum line, and extending away from the gum line to the degree that setting-up at least one prosthetic tooth to form a denture is possible. The gingival apron simplifies denture fabrication by practically eliminating the time consuming and difficult task of hand forming the gum line during the setup process. In the embodiment in FIG. 1, the gingival apron extends along the facial and lingual of the gum line and toward the inter proximal to the extent it will not interfere with the gingival apron of an adjacent prosthetic tooth and other structures during setup. It extends only slightly into the distal and mesial of the prosthetic tooth leaving a gap 24, and extends completely around the distal of the most posterior teeth in the upper and lower arches. The gap will allow the prosthetic tooth to be easily adjusted during setup without interference from an adjacent prosthetic tooth and other structures, and will allow setup material to move easily into the inter proximal area for forming the inter proximal denture gingiva and papillae. The gingival apron extends away from the gum line a short distance (about 0.5–5.0 mm) to the degree that setting-up at least one prosthetic tooth to form a denture is possible. It is sufficiently thick to provide structural support for the gingival apron (about 0.3–3.0 mm). It resembles a small gauge wax wire wrapped around and impressed against the facial and lingual surfaces of a denture tooth just under the gum line, not extending completely into the distal and mesial surfaces, and cut vertically on either end just short of the inter proximal plane 25 in FIG. 2.

Alternatively, it resembles a conventional denture which has been segmented along the inter proximal plane of each tooth leaving a small distance at the juncture between the gingival apron of an adjacent prosthetic tooth, hollowed out on the tissue-side of the denture base, and cut around the denture tooth at a uniform distance from the gum line. The size of the gingival apron can vary so long as it helps in the setup process. The setup process includes the formation of the gum line and the denture gingiva in the appearance of natural gum tissue.

The gingival apron is be formed of an appropriate material selected from the group consisting of wax, plastic, epoxy, rubber like material, silicone, polyurethane, acrylic plastic, thermoplastic, microwave curable plastic, light-curable plastic, two-stage curable plastic, shellac composition, any denture base material, and any suitable material. It is hard, resilient or pliable. It is opaque, translucent or transparent. The denture tooth is formed of an appropriate material selected from the group consisting of conventional denture tooth materials, plastic, porcelain, acrylic plastic, thermoplastic, microwave curable plastic, light curable plastic, a denture tooth material, and any suitable material.

Depending on the materials used, a slight variation in technique is required in the embodiments suggested herein. In this regard, the manufacturers recommendations for working with the materials should be employed in conjunction with the suggested embodiments. For example, a prosthetic tooth comprising a wax gingival apron can be setup in the conventional manner using the gingival apron as a guide to form the gum line.

Figures 3A, 3B:
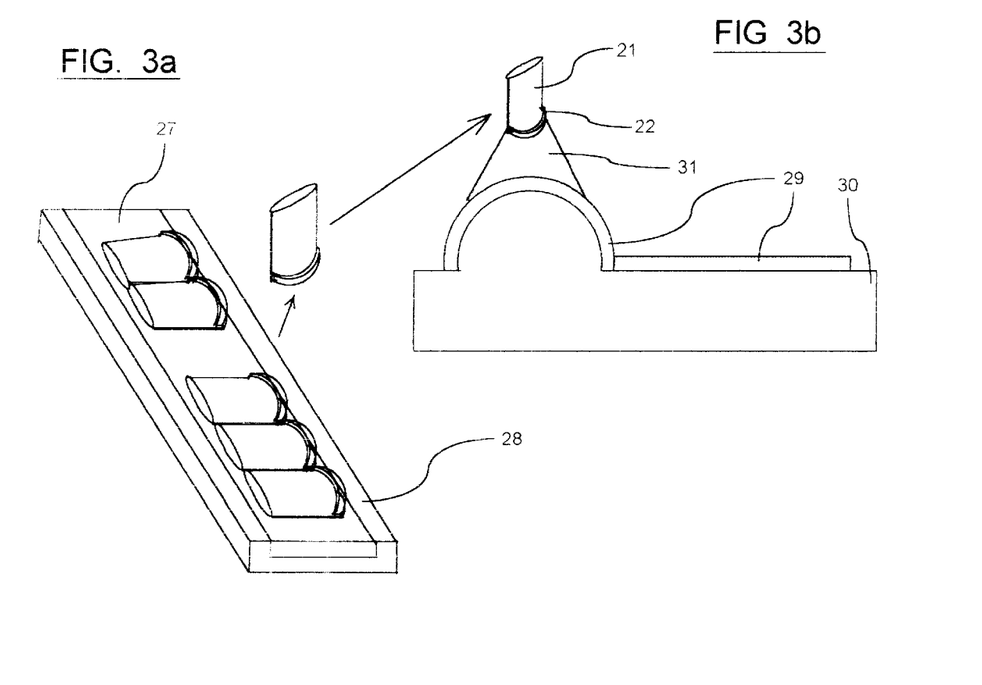

Referring to FIG. 3b, a denture base 29 is formed on a working platform 30. The posterior palatal seal should be formed at some stage in this process appropriate to the technique employed. The denture base is formed of an appropriate material selected from the group consisting of wax, plastic, epoxy, rubber like material, silicone, polyurethane, acrylic plastic, thermoplastic, microwave curable plastic, light-curable plastic, two-stage curable plastic, shellac composition, any denture base material, and any suitable material. It is hard, resilient or pliable. It is opaque, translucent or transparent. The working platform may already contain some teeth, where the working platform is selected from the group consisting of the mouth of a dental patient and a model representation of the mouth of a dental patient. The prosthetic teeth are setup on the denture base. Setup material 31, formed of an appropriate material selected from the group consisting of setup wax, wax, plastic, epoxy, rubber like material, silicone, polyurethane, acrylic plastic, thermoplastic, microwave curable plastic, light-curable plastic, two-stage curable plastic, shellac composition, any denture base material and any suitable material may be added to form a union between the prosthetic teeth and the denture base. It is hard, resilient or pliable. It is opaque, translucent or transparent. The prosthetic teeth are adjustable, interchangeable, and connectable with one another consistent with natural dentition. The prosthetic teeth are adjusted to fit the working platform and the denture is molded to imitate natural gum tissue. Since the prosthetic teeth contain a gingival apron which already defines the gum line, the tedious task of hand forming the gum line and some of the denture gingiva adjacent the denture tooth during setup is nearly eliminated. Just the simple formation of the denture gingiva and the papillae at the juncture between the prosthetic teeth may be required. Finally, the denture is stabilized, processed, and finished using the appropriate processing technique.

Again, referring to FIG. 3b, in a related embodiment, the denture is formed on a model representation 30 of the mouth of a dental patient using light-curable, materials. Most of the materials and equipment used for forming the denture in the present embodiment are commercially available from Dentsply International Inc., York, Pa. under the trademark TRIAD.

The model is formed of an appropriate material selected from the group consisting of a hard material, hard gypsum material, plaster, dental stone, plastic, low fusing metal, epoxy, and suitable hard material. If necessary, a thin smooth coating of model release agent (TRIAD Model Release Agent) is applied to the model on the areas where the denture base 29 will be adapted. The denture base is formed by adapting a sheet of light-curable denture base material (TRIAD VLC "sheet" material) on the model and trimming along the border to fit. The posterior palatal seal should be formed at some stage in this process appropriate to the technique employed. The denture base should be relatively uniform in thickness and should be sufficiently thick (about 1.5 mm) under the ridge lap portion of the prosthetic teeth. It may be necessary to grind the ridge lap areas of the prosthetic teeth or adjust the thickness of the edentulous area of the denture base. The denture base is now hardened by light-curing, and becomes part of the permanent denture base on which the prosthetic teeth are setup.

Next, referring to FIG. 3a, the prosthetic teeth are removed from the tooth card 27 comprising a gummy strip 28 and made ready to setup on the denture base to correspond to natural dentition and to fit an individual oral cavity in the manner described below. The gingival apron is made of a hardened dental plastic and will become part of the final denture. All the surfaces to be bonded are prepared by cleaning the surfaces and roughening them using a suitable dental bur. This may include the ridge lap surfaces of the prosthetic teeth and the edentulous denture base surface. Thereafter, a bonding agent (TRIAD VLC Bonding Agent) is applied on the surfaces to be bonded. The applied bonding agent is bench set and then light-cured.

At this stage, sufficient denture base material 31 (TRIAD VLC "rope" or Clear Pink Transheet) is applied to the ridge lap areas of the prosthetic teeth and/or to the edentulous surface of the denture base to form a union between the prosthetic teeth and the denture base. The prosthetic teeth are now setup on the denture base to fit an individual oral cavity, and the denture is contoured to conform in appearance to natural gum tissue. Much of the difficult task of forming the gum line is avoided since the prosthetic teeth already comprise a gum line. A small portion of the gingiva and the papillae in the space at the juncture between the prosthetic teeth may need to be contoured.

It may be desirable to "try-in" the denture, make the necessary adjustments, and stabilize the prosthetic teeth in the mouth by light-curing with an intra-oral light. Once the prosthetic teeth are in position and all of the adjustments have been made, a liquid air barrier coating (TRIAD Air Barrier Coating) is carefully brushed over the entire surface of the denture, and light-cured on both sides (light-curing with the tooth-side down first). Alternatively, the air barrier coating may be applied to the tooth-side of the denture while on the model and light-cured, and then removed from the model. Now, the air barrier coating may be applied to the tissue-side and light-cured again with the tissue-side up. The purpose of the air barrier coating is to ensure complete curing of the surface of the denture. The application of the air barrier coating may be avoided if a sealer coat is applied when the denture is finished. The sealer coat (ProCure Glaze made by Dental Resources, Inc., Delano, Minn.; Extoral Glaze Sealant made by Pro-Den Systems, Portland, Oreg.; or Pala-Seal made by Heraeus Kulzer, Inc., Irvine, Calif.) will ensure complete curing and provide a permanent seal and glaze to the denture.

As another alternative, only the tooth-side of the denture is light-cured while on the model. Then the tissue-side is relined 39 in FIG. 7 (TRIAD Dualine or VLC High Flow reline material), border-molded, and stabilized in the mouth of the dental patient for a more precise fit. Now, the denture is removed from the mouth, brushed with the air barrier coating on the tissue-side and border area and light-cured with its tissue-side up. The purpose of the air barrier coating is to ensure complete curing of the surface of the denture.

It may be desirable to "try-in" again and adjust the denture a final time before finishing and polishing the denture using normal methods. Finally, a sealing coat may be applied to the denture and light-cured a final time to ensure a smooth and non-porous surface.

As a variation on the above technique, starting at the stage where sufficient denture base material is applied, a lesser amount of denture base material is applied, sufficient only to setup the prosthetic teeth on the denture base to fit an individual oral cavity, but not enough to contour the denture surface to conform in appearance to natural gum tissue.

The prosthetic teeth are setup on the denture base. Any excess denture base material extruding from under the prosthetic teeth is removed or contoured under the prosthetic teeth leaving room on the denture surface for a sufficiently thick layer of denture base material to be applied later for contouring the surface of the denture to the appearance of natural gum tissue. It may now be desirable to "try-in", make the necessary adjustments, and stabilize the denture in the mouth with an intra-oral light. After all of the adjustments have been made, the denture is light-cured without an air barrier coating. Again, it may be necessary to prepare the surface areas of the denture for receiving additional material. At this stage, the denture may be replaced on the model and a layer of denture base material (TRIAD VLC "sheet") is added to the desired surface areas of the denture and contoured to imitate natural gum tissue. A liquid air barrier coating (TRIAD Air Barrier Coating) is brushed over the entire top surface of the denture and light-cured while on the model. Now, the denture is removed from its model, brushed with the air barrier coating on the tissue-side and light-cured with its tissue-side up. The purpose of the air barrier coating is to ensure complete curing of the surface of the denture. Again, the application of the air barrier coating may be avoided if a sealer coat is applied when the denture is finished.

As another alternative, before curing the tissue side of the denture, the denture is relined (TRIAD Dualine or VLC High Flow reline material), border molded, and stabilized in the mouth of the dental patient for a more precise fit. Now, the denture is removed from the mouth, brushed with the air barrier coating on the tissue-side and border area and light-cured with its tissue-side up. The purpose of the air barrier coating is to ensure complete curing of the surface of the denture.

It may be desirable to "try-in" and adjust the denture a final time before finishing and polishing the denture using normal methods. Finally, a sealing coat is applied to the entire surface of the denture base and light-cured a final time on both sides to ensure a smooth and non-porous surface.

As an alternative to applying a sealer coat or as an additional layer on the denture base before the sealer coat is applied, a thin layer of orthodontic gel (TRIAD Orthodontic Gel) may be applied to the surface of the denture base and cured. Again, the application of an air barrier coating may be avoided if a sealer coat is applied on the orthodontic gel.

b) Joining means

The prosthetic tooth may comprises at least one joining means, chemical or mechanical, for joining at least one denture tooth to a gingival apron, for joining at least one prosthetic tooth to a denture base, for joining prosthetic teeth together, for joining at least one prosthetic tooth to something, or for joining at least one prosthetic tooth. For example, the denture tooth may contain holes 26 in FIG. 2 below the gum line, for joining the gingival apron to the denture tooth. Alternatively, they may be joined by a chemical means.

Referring to FIG. 3a, prosthetic teeth may be made in a variety of molds and shades, corresponding to natural human dentition, and may comprise at least one joining means, such as a tooth card comprising the tooth card 27 and a gummy strip 28, for joining at least one prosthetic tooth. The prosthetic teeth are held in place on the tooth card by the gummy strip. The tooth card may be formed of an appropriate material selected from the group consisting of a rigid material, plastic, metal and wood. The gummy strip may be formed of an appropriate material selected from the group consisting of a tacky material, soft wax, and adhesive.

Figures 4A, 4D:
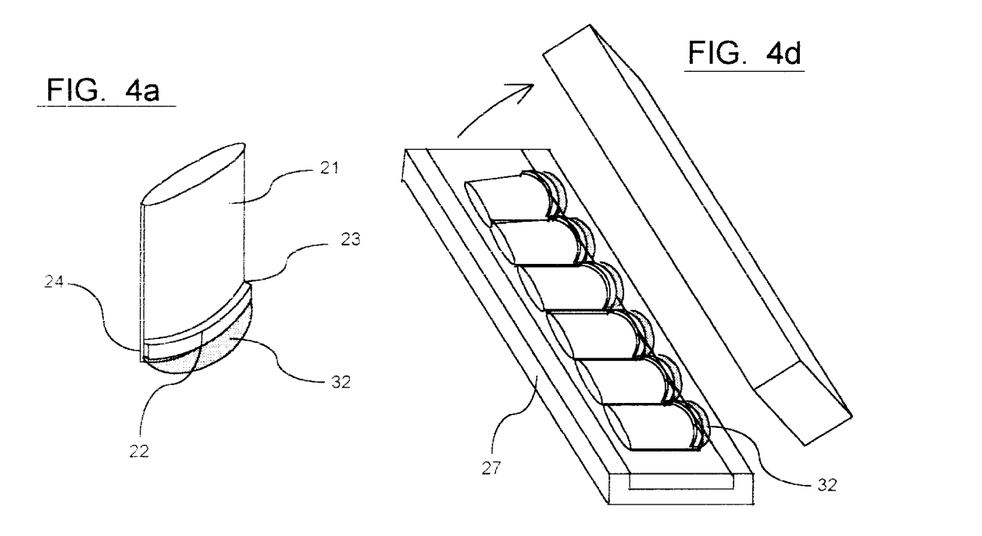
FIG. 4a is a side view of a prosthetic tooth comprising a denture tooth, a gingival apron and a pliable base
FIG. 4d is a perspective view of a two part tooth card comprising prosthetic teeth
Figures 4B, 4C:
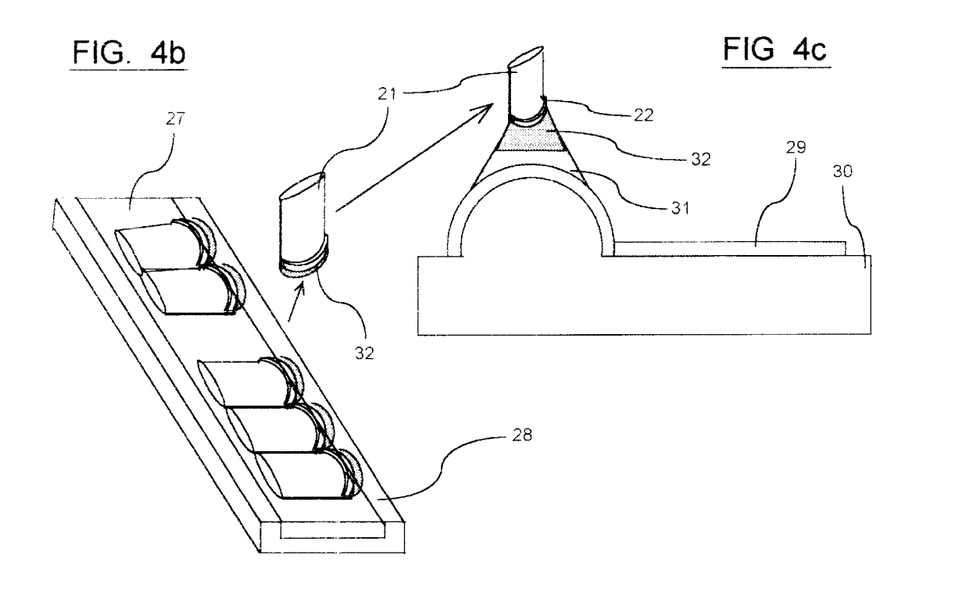

As an additional aid to setting-up, the denture teeth may comprise at least one joining means, such as a pliable base 32 in FIG. 4a, below the gum line and under the gingival apron on the tissue-side, for joining at least one denture tooth. Denture teeth may be joined to a tooth card 27, as illustrated in FIG. 4b. The tooth card may not comprise a gummy strip if the denture teeth already comprise a pliable or tacky base which will hold them in place or if the tooth card conforms to the shape of the denture teeth offering them sufficient support. The tooth card may be rectangular in shape and the denture teeth may be disposed on the tooth card in natural order ready to be set-up on a denture base. Alternatively, the tooth card may be formed in two parts FIG. 4d. The bottom part in contact with the tissue-side of the denture teeth may be rectangular and molded to form-fit and support the tissue-side of the denture teeth. The top part of the tooth card may be shaped to form-fit and support the tooth-side of the denture teeth. Both top and bottom parts of the tooth card may be shaped to fit each other so as to form a seal.

The pliable base may also act as a joining means for joining at least one denture tooth to a denture base, as illustrated in FIG. 4c, using normal set-up and processing techniques, or one of the techniques in the embodiments described herein. When denture teeth are set-up on the denture base, they may be manipulated on their pliable base to conform to the particular oral cavity. The denture is formed to appear natural. Little or no additional set-up material may be needed since the pliable base may serve the same function. Once the denture is in the desired form, the denture may be stabilized, processed, and finished. The pliable base may be formed of an appropriate material selected from the group consisting of wax, plastic, epoxy, rubber like material, silicone, polyurethane, acrylic plastic, thermoplastic, micro-wave curable plastic, light-curable plastic, two-stage curable plastic, shellac composition, any denture base material, and any suitable material. It may be hard, resilient, and/or pliable. It may be opaque, translucent, and/or transparent.

Figure 5A:
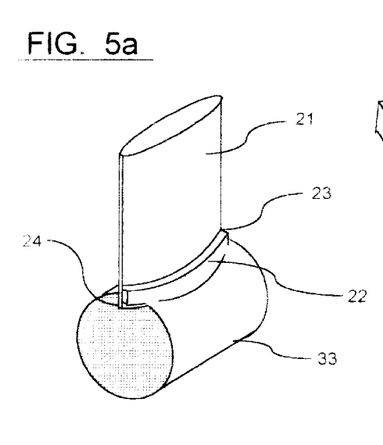
FIG. 5a is a side view of a prosthetic tooth comprising a denture tooth, a gingival apron and a rod shaped pliable base FIG. 5b prosthetic teeth comprising a rod shaped pliable base on a tooth card FIG. 5c a cross sectional view showing parts of a denture on a working platform
Figures 5B, 5C:
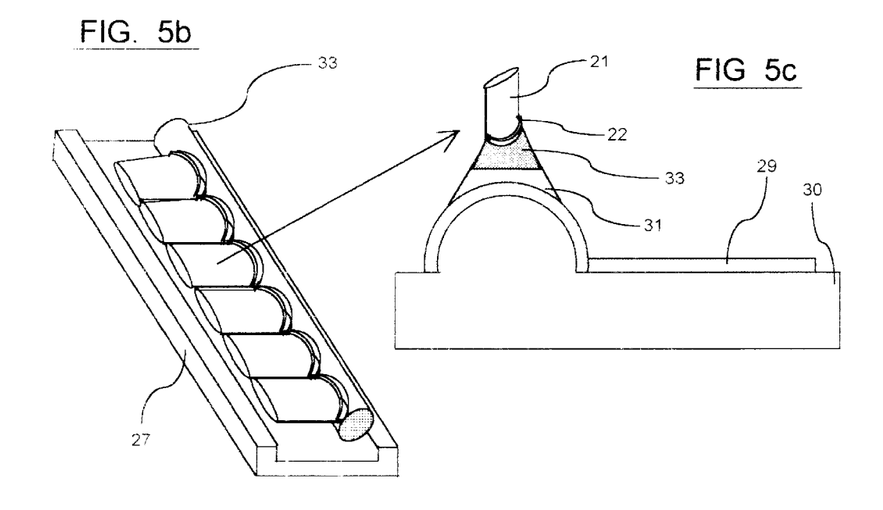
Figure 5D:
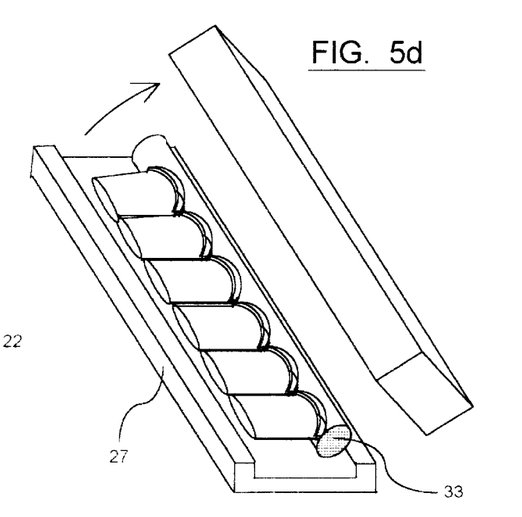
FIG. 5d is a perspective view of a two part tooth card comprising prosthetic teeth on a rod shaped pliable base

The pliable base may comprise a rod shaped base 33 in FIG. 5a, wherein at least one denture tooth is disposed on the rod shaped base, for joining at least one denture tooth. The rod shaped base, about the circumference of a pencil may extend to the outer interproximal planes 25 in FIG. 5b, of the outer most denture tooth in a set of at least one denture tooth. Denture teeth may be joined to a tooth card 27, as illustrated in FIG. 5b. The tooth card may not comprise a gummy strip if the denture teeth already comprise a pliable or tacky base which will hold them in place or if the tooth card conforms to the shape of the denture teeth and/or pliable base offering them sufficient support. The tooth card may be formed in a shape to conform to the rod shaped base. In this case the tooth card may be formed in a semicircular rod shape and may be linear in length or curved consistent with the human arch. The denture teeth are disposed on the rod shaped base in natural order ready to be set-up on a denture base. Alternatively, the tooth card may be formed in two parts FIG. 5d. The bottom part in contact with the rod shaped base may be rectangular and molded to form-fit and support the bottom part of the rod shaped base. The top part of the tooth card may be shaped to form-fit and support the tooth-side of the denture teeth and the top part of the rod shaped base. Both top and bottom parts of the tooth card may be shaped to fit each other so as to form a seal.

The rod shaped base may also act as a joining means for joining at least one denture tooth to a denture base, as illustrated in FIG. 5c, using normal set-up and processing techniques, or one of the techniques described in the embodiments herein. When denture teeth are set-up on the denture base, they may be manipulated on their pliable rod shaped base to conform to the particular oral cavity. The denture is formed to appear natural. Little or no additional set-up material may be needed since the pliable rod shaped base may serve the same function. Once the denture is in the desired form, the denture may be stabilized, processed, and finished. In addition to being able to be set-up individually, the denture teeth comprising a rod shaped base, may be set-up on a denture base in groups. The rod shaped base may be formed of an appropriate material selected from the group consisting of wax, plastic, epoxy, rubber like material, silicone, polyurethane, acrylic plastic, thermoplastic, micro-wave curable plastic, light-curable plastic, two-stage curable plastic, shellac composition, any denture base material, and any suitable material. It may be hard, resilient, and/or pliable. It may be opaque, translucent, and/or transparent.

c) General Features

Figure 6:
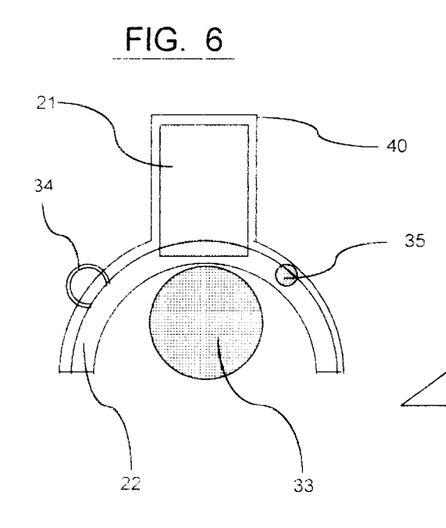
FIG. 6 is a side view of a prosthetic tooth comprising various parts FIG. 7 an adjustable alignment plate comprising guides releasably attached in centric registry to the prosthetic teeth FIG. 8a a denture tooth comprising a groove or a notch formed along the gum line FIG. 8b a denture tooth comprising a highly defined or large gingival bulge along the gum line

Prosthetic teeth may comprise a removable clear flexible film 40 in FIG. 6, on the tooth-side of denture teeth, formed of an appropriate material selected from the group consisting of plastic, polyethylene, polyvinylydine chloride, polyolefin, and a clear film. The film is securely affixed to the exterior surface of each prosthetic tooth. The clear flexible film acts to join the prosthetic teeth and to contain the pliable denture base material within the denture structure when it is squeezed and flows up through the gap and into the interproximal space during the set-up, fitting, and adjusting process. Additionally, the prosthetic teeth may comprise the clear flexible film on the tissue side as well as the tooth side. The clear flexible film is removed from the tissue side before fitting to the working platform and removed from the tooth side before applying additional denture base material, after stabilizing or light curing.

As an aid to adjusting and fitting, each prosthetic tooth may contain a small knob-shaped, button-shaped, or loop-shaped protrusion on an accessible surface for catching with an instrument and moving the prosthetic tooth 34 in FIG. 6.

The protrusion may be formed of an appropriate material selected from the group consisting of metal, wax, plastic, porcelain, epoxy, rubber like material, silicone, polyurethane, acrylic plastic, thermoplastic, microwave curable plastic, light-curable plastic, two-stage curable plastic, shellac composition, any denture base material, and any suitable material. It may be opaque, translucent, and/or transparent.

The prosthetic teeth may be joined by a deflectable string-shaped structure 35 in FIG. 6 formed of an appropriate material selected from the group consisting of metal, plastic, rubber like material, silicone, wax, epoxy, polyurethane, shellac composition, wire, fiber, string, chain, cable, and a net-shaped structure. It may be opaque, translucent, and/or transparent. It is securely and unobtrusively attached to each prosthetic tooth to allow the prosthetic tooth to be adjusted to accommodate an individual oral cavity.

A flexible netting (not shown) may be applied to the tissue-side of the denture and/or embedded within the denture base for additional strength, support, and/or aid in fabrication. The netting may be formed of an appropriate material selected from the group consisting of metal, plastic, rubber like material, silicone, wax, epoxy, polyurethane, shellac composition, wire, fiber, string, chain, cable, and a net-shaped structure. It may be opaque, translucent, and/or transparent.

Light-curable materials should be protected from light to prevent premature curing. For example, the tooth cards and/or other packaging may be formed of opaque materials and sealed in an opaque manner FIGS. 4d and 5d.

Figure 7:
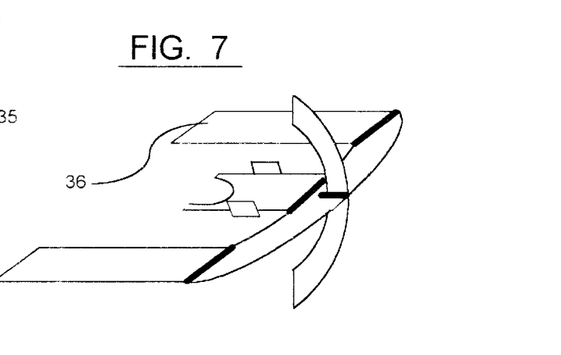

As another option, prosthetic teeth may be adjusted to the desired occlusal relationship by an adjustable alignment plate which may comprise horizontal and vertical guides releasably attachable in centric registry to the occlusal and/or the facial part of the prosthetic teeth 36 in FIG. 7. The alignment plate may be made in various sizes, shapes, and configurations. It may be sufficiently thin and/or designed so as not to interfere with the occlusal and/or lateral relationship of the prosthetic teeth and/or the fabrication of the denture. The adjustable alignment plate may be formed of an appropriate material selected from the group consisting of metal, wax, plastic, porcelain, epoxy, rubber like material, silicone, polyurethane, acrylic plastic, thermoplastic, microwave curable plastic, light-curable plastic, two-stage curable plastic, shellac composition, any denture base material, and any suitable material. It may be opaque, translucent, and/or transparent.

As another alternative, a complete upper or lower set of prosthetic teeth may be held in a fixed occlusal relationship by an alignment plate whereby the dentures are removably fixed to the alignment plate. The alignment plate may be removed after the denture is fitted. The alignment plate may be removably attached to the occlusal and/or the facial part of the prosthetic teeth. It may be sufficiently thin and/or designed so as not to interfere with the occlusal and/or lateral relationship of the prosthetic teeth and/or the fabrication of the denture.

Figures 8A, 8B:
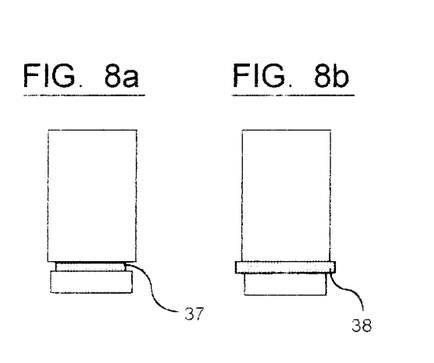
Figure 9:
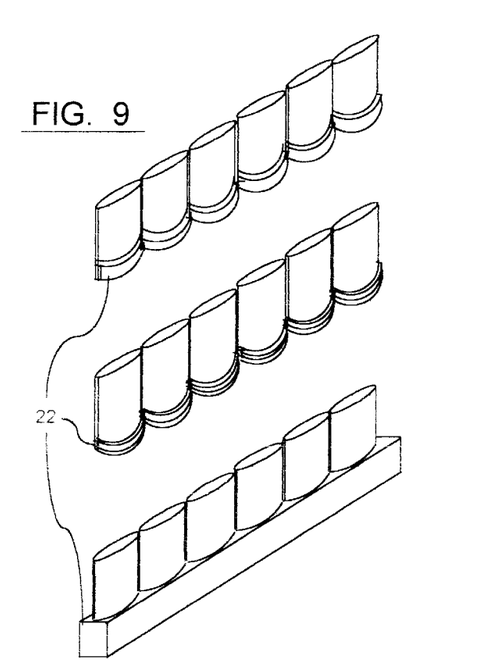
FIG. 9 shows a plurality of denture teeth joined by a gingival apron.

As an alternative guide to forming the gum line, the denture tooth may comprise a groove or a notch formed along the gum line to act as a guide in forming the gum line 37 in FIG. 8a. As another alternative, the denture tooth may comprise a highly defined or large gingival bulge along the gum line to act as a guide in forming the gum line 38 in FIG. 8b.

In an additional embodiment, a preformed gingival apron conforming in appearance to natural gum tissue extends along at least part of at least one denture tooth at a gum line, wherein the at least one denture tooth is embedded in the preformed gingival apron to form a unitary structure conforming in appearance to at least part of a denture. The preformed gingival apron comprising a full arch or at least part of an arch of denture teeth may be setup in one piece of may be segmented to accommodate an individual oral cavity. A preformed gingival apron comprising only a single denture tooth extends the disto-mesial length of the denture tooth and is setup individually.

The invention may be embodied in other specified forms without departing from the spirit or essential characteristics thereto. The present embodiments are therefore to be considered in all respects as illustrative and not restrictive, the scope of the invention being indicated by the appended claims rather than the foregoing description, and all changes which may come within the meaning and range of equivalency of the claims are therefore intended to be embraced therein.

I claim:

1. A dental device, comprising at least one prosthetic tooth, said at least one prosthetic tooth comprising:
    (a) at least one denture tooth, and
    (b) means for setting up said denture tooth on a denture base and for forming a gum line on said denture base, said means comprising a preformed gingival apron conforming in appearance to natural gum tissue, said apron joined to and extending along at least part of said denture tooth at a gum line, said apron extending away from the gum line so that the prosthetic tooth may be set up to form a denture and gum line in a single step.

2. The dental device of claim 1 further comprising at least one means for joining said at least one denture tooth to said gingival apron, said at least one joining means being selected from the group consisting of a mechanical means and a chemical means.

3. The dental device of claim 1 further comprising a pliable base, said pliable base adapted to join said at least one prosthetic tooth to a denture base.

4. The dental device of claim 1, further comprising at least one means for joining said at least one prosthetic tooth to at least one other prosthetic tooth, selected from the group consisting of a film affixed to an exterior surface of said at least one prosthetic tooth, and said preformed gingival apron.

5. The prosthetic tooth of claim 1, further comprising means for adjusting and fitting said at least one prosthetic tooth, said means for adjusting and fitting being selected from the group consisting of a string shaped structure, a protrusion, and an adjustable alignment plate.

6. The prosthetic tooth of claim 5, wherein said protrusion is selected from the group consisting of a knob-shaped protrusion, a button-shaped protrusion and a loop-shaped protrusion.

7. The prosthetic tooth of claim 1, further comprising a tooth card, said at least one prosthetic tooth being removably affixed to said tooth card.

8. A denture comprising:
    (a) a denture base, and
    (b) at least one prosthetic tooth,
said at least one tooth comprising at least one denture tooth and means for setting up said at least one denture tooth on said denture base and for forming a gum line on said denture base, said means comprising a preformed gingival apron conforming in appearance to natural gum tissue, said apron joined to and extending along at least part of said at least one denture tooth at a gum line, said apron extending away from the gum line so that at least one prosthetic tooth may be set up to form a denture and gum line in a single step.

9. The denture of claim 8, further comprising a netting attached to said denture base.

10. The denture of claim 9, wherein said netting is attached to the underside of the denture base.

11. The denture of claim 9, wherein said netting is embedded in said denture base.

12. The denture of claim 8, wherein said at least one prosthetic tooth further comprises at least one means for joining said at least one denture tooth to said gingival apron, said at least one joining means being selected from the group consisting of a mechanical means and a chemical means.

13. The denture of claim 8, wherein said at least one prosthetic tooth further comprises a pliable base, said pliable base adapted to join said at least one prosthetic tooth to said denture base.

14. The denture of claim 8, wherein said at least one prosthetic tooth further comprises at least one means for joining said at least one prosthetic tooth to at least one other prosthetic tooth, selected from the group consisting of a film affixed to said at least one prosthetic tooth, and said preformed gingival apron.

15. The denture of claim 8, further comprising means for adjusting and fitting said at least one prosthetic tooth, said means for adjusting and fitting being selected from the group consisting of a string shaped structure, a protrusion and an adjustable alignment plate.

16. The denture of claim 15, wherein said protrusion is selected from the group consisting of a knob-shaped protrusion, a button-shaped protrusion and a loop-shaped protrusion.

17. The denture of claim 8, further comprising a tooth card, said at least one prosthetic tooth being removably affixed to said tooth card.

18. A method of making a denture, said method comprising the steps of:
(a) providing a working platform, said platform selected from the group consisting of the mouth of a patient and a model representation of the mouth of a patient,
(b) providing at least one prosthetic tooth, said at least one prosthetic tooth comprising at least one denture tooth and means for setting up said at least one denture tooth on a denture base and for forming a gum line on said denture base, said means comprising a preformed gingival apron conforming in appearance to natural gum tissue, said preformed gingival apron joined to and extending along at least part of said at least one denture tooth at a gum line, said apron extending away from said gum line so that the at least one prosthetic tooth may be set up to form a denture and gum line in a single step,
(c) providing a denture base,
(d) setting up said at least one prosthetic tooth on said denture base to form a denture,
(e) shaping said denture, and
(f) processing and finishing said denture.

19. The method of making a denture according to claim 18, further comprising the step of attaching a netting to said denture base.

20. The method of making a denture according to claim 18, further comprising the step of providing at least one means for joining said at least one prosthetic tooth to other prosthetic teeth, said joining means selected from the group consisting of a film affixed to an exterior surface of said at least one prosthetic tooth, and said preformed gingival apron.

* * * * *